(12) United States Patent
James et al.

(10) Patent No.: US 9,155,523 B2
(45) Date of Patent: Oct. 13, 2015

(54) METHOD OF DETECTING AND PREDICTING OVULATION AND THE PERIOD OF FERTILITY

(71) Applicant: Fertility Focus Limited, Dorchester, Dorset (GB)

(72) Inventors: Michael Howard James, Dorchester (GB); Toby Grahame Knowles, Bristol (GB)

(73) Assignee: FERTILITY FOCUS LIMITED, Warwick (GB)

( * ) Notice: Subject to any disclaimer, the term of this patent is extended or adjusted under 35 U.S.C. 154(b) by 0 days.

(21) Appl. No.: 13/953,360

(22) Filed: Jul. 29, 2013

(65) Prior Publication Data

US 2013/0310704 A1  Nov. 21, 2013

Related U.S. Application Data

(63) Continuation of application No. 13/933,417, filed on Jul. 2, 2013, which is a continuation of application No. 12/440,231, filed as application No. PCT/GB2007/003344 on Sep. 5, 2007, now Pat. No. 8,496,597.

(30) Foreign Application Priority Data

Sep. 5, 2006  (GB) .................................... 0617451.0

(51) Int. Cl.
*A61B 10/00* (2006.01)
*A61B 5/00* (2006.01)
*A61B 5/01* (2006.01)

(52) U.S. Cl.
CPC ............ *A61B 10/0012* (2013.01); *A61B 5/0008* (2013.01); *A61B 5/01* (2013.01); *A61B 5/6802* (2013.01); *A61B 5/7278* (2013.01); *A61B 2010/0019* (2013.01)

(58) Field of Classification Search
CPC .................................................. A61B 10/0012
USPC .......... 600/300, 474, 549, 551; 374/121, 129, 374/130, 133; 705/2; 604/19
See application file for complete search history.

(56) References Cited

U.S. PATENT DOCUMENTS

| 4,151,831 A | 5/1979 | Lester |
| 4,370,727 A | 1/1983 | Bellet |

(Continued)

FOREIGN PATENT DOCUMENTS

| CH | 651191 A5 | 9/1985 |
| DE | 3342251 A1 | 5/1985 |

(Continued)

OTHER PUBLICATIONS

Official Action dated Apr. 2, 2013 issued in related Japanese Application No. JP2009-527197 and English language summary thereof. (3 pages).

(Continued)

*Primary Examiner* — Brian Szmal
(74) *Attorney, Agent, or Firm* — Carter, DeLuca, Farrell & Schmidt, LLP; Robert P. Michal, Esq.

(57) ABSTRACT

Methods of detecting and predicting ovulation and a period of fertility include determining a series of measures indicative of the basal body temperature of a female human user to identify a temperature change event. The method includes obtaining, within a first 24 hour period, a plurality of first readings of the temperature of the female human user at intervals over a first extended period of at least an hour. The plurality of first readings are then processed to determine at least one first representative temperature reading representative of the basal body temperature of the user for the first extended period and the at least one first representative temperature reading is stored. The method is repeated for at least second and third 24 hour periods and the representative temperature readings are provided for analysis to identify a temperature change event for the female human user.

18 Claims, 4 Drawing Sheets

(56) References Cited

U.S. PATENT DOCUMENTS

| | | | |
|---|---|---|---|
| 4,443,851 A | 4/1984 | Lin | |
| 4,465,077 A | 8/1984 | Schneider | |
| 4,475,158 A | 10/1984 | Elias | |
| 4,509,531 A | 4/1985 | Ward | |
| 4,549,819 A | 10/1985 | Muramoto et al. | |
| 4,651,137 A | 3/1987 | Zartman | |
| 4,676,254 A | 6/1987 | Frohn | |
| 4,771,791 A | 9/1988 | Kubouchi | |
| 4,929,089 A | 5/1990 | Tsuchida | |
| 5,050,612 A | 9/1991 | Matsumura | |
| 5,209,238 A | 5/1993 | Sundhar | |
| 5,246,292 A * | 9/1993 | Gal et al. | 374/121 |
| 5,816,706 A | 10/1998 | Heikkila et al. | |
| 6,220,750 B1 | 4/2001 | Palti | |
| 6,270,252 B1 | 8/2001 | Siefert | |
| 6,351,217 B1 | 2/2002 | Kuhn | |
| 6,478,748 B1 | 11/2002 | Kuhn et al. | |
| 6,595,929 B2 | 7/2003 | Stivoric et al. | |
| 6,794,990 B2 | 9/2004 | Tseng | |
| 6,814,706 B2 | 11/2004 | Barton et al. | |
| 7,015,826 B1 | 3/2006 | Chan et al. | |
| 7,148,803 B2 | 12/2006 | Bandy et al. | |
| 7,285,090 B2 | 10/2007 | Stivoric et al. | |
| 2002/0010390 A1 | 1/2002 | Guice et al. | |
| 2002/0016553 A1 | 2/2002 | Tamaki et al. | |
| 2003/0069714 A1 | 4/2003 | Wigley et al. | |
| 2003/0210146 A1 | 11/2003 | Tseng | |
| 2004/0102815 A1 | 5/2004 | Balczewski et al. | |
| 2004/0152957 A1 | 8/2004 | Stivoric | |
| 2004/0171964 A1 | 9/2004 | Heitz | |
| 2004/0215098 A1 | 10/2004 | Barton et al. | |
| 2005/0059870 A1 | 3/2005 | Aceti | |
| 2005/0092177 A1 | 5/2005 | Bonchonsky et al. | |
| 2005/0096558 A1 | 5/2005 | Friedman et al. | |
| 2005/0101841 A9 * | 5/2005 | Kaylor et al. | 600/300 |
| 2005/0245839 A1 | 11/2005 | Stivoric et al. | |
| 2006/0070650 A1 | 4/2006 | Fraden | |
| 2006/0173375 A1 | 8/2006 | Koch | |
| 2006/0224349 A1 | 10/2006 | Butterfield | |
| 2007/0191729 A1 | 8/2007 | Park et al. | |
| 2007/0276283 A1 | 11/2007 | Hung | |
| 2009/0234200 A1 | 9/2009 | Husheer | |
| 2011/0301493 A1 | 12/2011 | Husheer | |

FOREIGN PATENT DOCUMENTS

| | | |
|---|---|---|
| DE | 4213065 A1 | 10/1993 |
| DE | 4413881 A1 | 10/1995 |
| DE | 19852559 A1 | 5/2000 |
| DE | 19943456 A1 | 4/2001 |
| DE | 10335745 A1 | 3/2005 |
| DE | 10345282 B3 | 4/2005 |
| EP | 0195207 A2 | 1/1986 |
| EP | 0424102 A1 | 4/1991 |
| EP | 0476730 A1 | 3/1992 |
| EP | 0549081 A1 | 6/1993 |
| EP | 0746040 A1 | 12/1996 |
| EP | 0619123 A3 | 8/1997 |
| EP | 1495722 A1 | 1/2005 |
| EP | 1593946 B1 | 6/2011 |
| GB | 2077593 A | 12/1981 |
| GB | 2186977 A | 8/1987 |
| GB | 2416633 A | 2/2006 |
| JP | 09-122132 A | 5/1997 |
| JP | 2001-353157 A | 12/2001 |
| JP | 2001-353158 A | 12/2001 |
| JP | 2001-353159 A | 12/2001 |
| JP | 2001-353160 A | 12/2001 |
| JP | 2004163391 A | 6/2004 |
| JP | 2004325110 A | 11/2004 |
| JP | 2005164405 A | 6/2005 |
| JP | 2005521039 A | 7/2005 |
| JP | 2007-068839 A | 3/2007 |
| KR | 100682457 B1 | 2/2007 |
| WO | WO 87/02876 A2 | 5/1987 |
| WO | WO 01/84518 A1 | 11/2001 |
| WO | WO 03/078949 A1 | 9/2003 |
| WO | WO 2005/032338 A2 | 4/2005 |
| WO | WO 2005/092177 A1 | 10/2005 |
| WO | 2007/049157 A2 | 5/2007 |
| WO | WO 2007/077405 A2 | 7/2007 |
| WO | WO 2007/113825 A1 | 10/2007 |
| WO | WO 2008/029130 A2 | 3/2008 |
| WO | WO 2008/029130 A3 | 3/2008 |
| WO | WO 2008/035151 A2 | 3/2008 |
| WO | WO 2011/070577 A2 | 6/2011 |
| WO | WO 2011/070577 A3 | 6/2011 |

OTHER PUBLICATIONS

Submission in Opposition Proceedings dated Jun. 3, 2013 issued from the European Patent Office in related European Patent No. EP 2061380 (Application No. EP 07804149.8) (10 pages).

T.J. Doherty, et al., "Technical Note No. TN-00/2—Circad: Automated Analysis of Circadian Core Temperature Data," U.S. Army Research Institute of Environmental Medicine, Natick, MA., 2000 (52 pages).

Olsen, et al., "A data logger tag for the study of slaughter procedures in aquacultured salmon," Hydrobiologia, 1998, vol. 371/372, pp. 71-77.

Ciarcia, "Build a Low-Power Data Logger," Circuit Cellular Ink, 1990, vol. 15, pp. s12-s22.

Notice and Grounds of Opposition as filed in related EP Patent 2061380 on Feb. 20, 2012 by Opponent, Secerna LLP.

Coyne, M.D., et al., "Circadian rhythm changes in core temperature over the menstrual cycle: method for noninvasive monitoring," Am. J. Physiol. Regulatory Integrative Comp. Physiol. vol. 279 (2000), pp. R1316-R1320.

Davis, M.E., et al., "The Cause of Physiologic Basal Temperature changes in Women," J. Clin. Endocrinol. Metab., 1948, vol. 8, pp. 550-563.

Fertility Focus Limited, International Search Report and the Written Opinion of the corresponding PCT Application No. PCT/GB2007/003344, dated Jun. 24, 2008 (18 pages).

McCarthy, Jr., J.J. and Rockette, H.E., "A comparison of methods to interpret the basal body temperature graph," Fertility and sterility, vol. 39, No. 5 (May 1983), pp. 640-646.

Taylor, A., "Clinical review: ABC of subfertility—Extent of the problem," BMJ, vol. 327 (Aug. 23, 2003), pp. 434-436, downloaded from bmj.com on Feb. 10, 2009.

Taylor, A., "Clinical review: ABC of subfertility—Making a diagnosis," BMJ, vol. 327 (Aug. 30, 2003), pp. 494-497, downloaded from bmj.com on Feb. 10, 2009.

Van Marken Lichtenbelt et al., Evaluation of Wireless Determination of Skin Temperature Using iButtons, Journal of Physiology and Behavior, 2006, pp. 489-497, vol. 88, Elsevier.

De La Fuente Ruz et al., RFID Smart Temperature Sensor, Application in monitoring and traceability of hemoderivatives, Mar. 13, 2007, EU RFID Forum, Brussels, Belgium.

Wim Claes et al., Design of Wireless Autonomous Data Logger ICs, 2005, Springer of The Netherlands.

Notification of Transmittal of the International Search Report and the Written Opinion of the International Searching Authority, or the Declaration dated Sep. 26, 2014 issued in International Application No. PCT/GB2014/051976 along with PCT International Search Report dated Sep. 26, 2014 issued in PCT/GB2014/051976 along with the Written Opinion of the International Searching Authority (9 pages).

* cited by examiner

METHOD OF DETECTING AND PREDICTING OVULATION AND THE PERIOD OF FERTILITY

CROSS-REFERENCE TO RELATED APPLICATION

This is a Continuation of U.S. patent application Ser. No. 13/933,417, filed Jul. 2, 2013, which is a Continuation of U.S. patent application Ser. No. 12/440,231, filed Mar. 5, 2009, which is a national stage application of PCT/GB2007/003344, filed Sep. 5, 2007, which in turn claims foreign priority to GB Application No. 0617451.0, filed Sep. 5, 2006.

This is also a Continuation of U.S. patent application Ser. No. 12/440,231, filed Mar. 5, 2009, which is a national stage application of PCT/GB2007/003344, filed Sep. 5, 2007, which in turn claims foreign priority to GB Application No. 0617451.0, filed Sep. 5, 2006.

The entire disclosure of each of the above-mentioned applications is incorporated herein by reference.

BACKGROUND INFORMATION

Ovulation

Ovulation, the release of an oocyte from an ovary of a female animal, is an important step of female reproductive biology because it is required in order that the oocyte may be fertilized by male sperm.

In archetypical human females, ovulation takes place on approximately day 14 of the typically 28 day menstrual cycle. However, only approximately 10% of women regularly ovulate on day 14 of a 28 day cycle. The cycle length and day of ovulation within a single cycle can vary between women and, usually to a lesser extent, from time to time in a single woman. Variation in the cycle length of an individual woman includes both fluctuations from one cycle to the next and longer term "drifts" in cycle length which take place over several years and may be part of the ageing process.

In non-human mammals, the biology of ovulation varies considerably. Some animals, for example, dogs and cattle, conform approximately to the human model and exhibit a non-seasonal pattern of ovulation at regular intervals. Other animals (for example, sheep, rabbits, ferrets) require environmental cues, for example changing day length or the presence of males, in order for ovulation to be triggered. Other animals, for example mice, only ovulate in response to copulation. There are many circumstances, both in the fields of medicine and veterinary practice, where it is useful to know if ovulation has taken place.

In general terms, the ability to detect the presence or absence of ovulation is useful both in the diagnoses of disorders of ovulation and in providing information about likely fertility which can be used to choose suitable timing of sexual intercourse in order to increase or decrease the odds of pregnancy resulting in accordance with the wishes of the woman, in the field of human medicine, or in accordance with the wishes of the farmer or veterinarian in the field of animal husbandry. Furthermore, information about the timing of ovulation may be used to choose suitable timing of fertility treatments such as intrauterine insemination (IUI), artificial insemination or removal of ova for in vitro fertilisation.

It has been estimated that one in six human couples have an unwanted delay in conception (Taylor (2003) BMJ 327:434-436). Most of those couples do not have absolute infertility (that is, no chance of conception) but rather subfertility with a reduced chance of conception because of one or more factors in either or both partners.

As part of the diagnoses of subfertility one of the key questions which the clinician asks is 'does the woman ovulate?' In addition to answering the above question, knowing or predicting when the woman ovulates is also useful in cases of subfertility because it allows the couple and/or the physician involved in providing fertility enhancement treatment to time their sexual intercourse and/or therapeutic intervention so as to maximise the chances of conception.

Knowledge of the time of ovulation and thereby knowledge of a woman's fertility can also be useful where a woman in a sexual relationship wishes to avoid conception. By limiting unprotected sex to times when the woman is unlikely to be fertile, unwanted pregnancies can be avoided. Such a 'natural' method of contraception may be especially attractive to couples who have medical, religious or other reasons for avoiding the use of alternative contraception.

In the veterinary fields, animal sub-fertility may be a problem, particularly if the animals in question are commercially valuable (for example race horses, cattle, companion animals) or members of an endangered species. Additionally in many animal species stud fees and/or semen samples for artificial insemination are costly. There is therefore a need to limit those interventions to times when the female is fertile.

The Human Ovulatory Cycle

The cyclic changes in ovarian activity are controlled by the secretion of two hormones by the pituitary gland, follicle stimulating hormone (FSH) and luteinizing hormone (LH) under the control of the hypothalamus.

During the second half of the proceeding cycles, high levels of oestradiol (oestrogen) and progesterone (progestogen) act via the hypothalamus to suppress FSH and LH production by the pituitary gland. At the end of the proceeding cycle a decrease in production of oestradiol and progesterone by the corpus luteum removes suppression of the hypothalamus and FSH levels start to rise. Once a threshold is met, FSH stimulates a group of ovarian follicles into growth.

The dominant follicle continues to grow towards ovulation and as it does so it produces increasing amounts of oestradiol. This leads to a fall in FSH which removes support for non-dominant follicles and increases the dominant follicle's receptivity to LH. The high oestradiol level causes the pituitary gland to release a large surge of LH. This peak of LH triggers the rupture of the follicle and release of the oocyte (ovulation) approximately 37 hours after the beginning of the surge of LH or approximately 17 hours after its peak.

The remains of the ruptured follicle become the corpus luteum which produces progesterone which causes an abrupt change in the characteristics of the cervical mucus so as to make it impenetrable to sperm. A decrease in progesterone towards the end of the cycle causes the bleeding of menstruation.

Related changes in hormone levels are seen in veterinary species, the levels and timing of events altering from species to species—all result in a corresponding release of an ovum into the fallopian tube following rupture of a mature follicle.

By convention the human ovulatory cycle (also known as the menstrual cycle) considered to start from the first day of menses (day 1) and continue until the first day of menses of the following cycle takes place.

Detection of Ovulation

The UK Royal College of Obstetricians & Gynaecologists guidelines for investigating whether ovulation is likely to take place includes checking mid-luteal phase progesterone 7 days before expected menses. Other investigations which may be carried out include measuring LH, FSH and oestradiol concentrations in early follicular phase (days 2 to 6), (Taylor (2003) BMJ 327:494-497).

Measurement of hormone levels typically requires the drawing of a blood sample or the use of urine tests. These methods of measurement have the drawback that they require medical intervention and that each individual test costs money.

Urine tests additionally suffer from poor reliability because urine production rates are subject to unpredictable variations that lead to variations in hormone concentrations in the urine in the bladder.

Whilst blood tests may be highly suitable for occasional diagnostic testing, they have significant drawbacks if they are to be used for long periods of time. Several surrogate markers of ovulation in human female that are more suitable for home use and for sustained monitoring have been identified. The first of these involves the woman checking the consistency of her cervical mucus. The second involves the woman recording her body temperature. Body temperature is a widely used surrogate marker for the detection of ovulation. It is known that the LH peak which occurs just before ovulation causes a rise in body temperature, (see David M E & Fugo (1948), The cause of physiologic basal temperature changes in women Clin. Endocrinol. 8:550-563 and Coyne et al, (2000)) Circadian rhythm changes in core temperature over the menstrual cycle: method for non-invasive monitoring, A.L.C.J. Physiol. Regulatory Integrative Comp. Physiol. 279:1316-1320. The detection of that rise is used widely as a surrogate marker for ovulation.

The oestradiol rise before ovulation causes a slight and broad dip in body temperature before the LH-associated rise, (David & Fugo ibid) This dip is not currently used as a marker of ovulation because it is difficult to measure accurately, mainly because it is of low magnitude.

Temperature readings are typically taken once a day under the tongue with a standard mercury, spirit or electronic medical thermometer, although temperature may also be measured on the skin surface, under the armpit, in the ear or at any other suitable site. WO 03/078949 discloses a retrievable indwelling thermometer which may be used to measure rectal or intravaginal temperature over an extended period of time.

Current methods of taking and analysing temperature measurements in order to predict or detect ovulation have several drawbacks. Infrequently-taken temperatures may not be representative of the true basal body temperature and using a thermometer to take multiple temperatures manually is time consuming and inconvenient.

The device of WO 03/078949 may be used to take multiple temperature readings over a time period, but nevertheless the temperatures taken may be unrepresentative of the true basal body temperature for a number of reasons including the time-lag required for the temperature reading device to warm up after initial insertion, and non-relevant temperature changes which come about due to inadvertent or deliberate removal, urination and diurnal temperature variations. Such inaccuracies in temperature readings cause inaccuracies in the detection of the LH-associated temperature peak and prevent the detection of the oestradiol-associated temperature dip.

DE 3342251 speculates about a device for measuring the temperature in a female in order to detect temperature changes associated with ovulation. It is suggested that prediction of the timing of ovulation in the subsequent cycle may be earned out by counting forward in time from the start of the previously detected ovulatory cycle. The device disclosed in DE 3342251 measures multiple temperatures over at least part of several days. The specification does not disclose any real data (for example the data shown in the figure is obviously contrived). It is suggested that in order to minimise the effects of fluctuations in temperature that are irrelevant to detecting ovulation, maxima and/or minima curves be calculated and analysed for the presence of temperature changes indicative of ovulation. The Inventors of the present invention consider that the use of maxima or minima curves as disclosed in DE 3342251 is unlikely to work well because those variables are highly susceptible to irrelevant temperature changes (outlier data values).

GB 2077595 is directed mainly to monitoring the body temperatures of cows rather than humans. En fact page 3, column 1, lines 62 to 65 suggests that reliable detection of ovulation in humans by temperature measurement cannot be carried out. In terms of processing of temperature readings it is taught that temperature may be used for the detection of oestrus and for the detection of fever associated with poor health. It is also taught that a cow's temperature is partially dependent on ambient conditions and on individual characteristics of a particular cow. The recording of long term temperature readings in a cow is carried out in order to solve a different problem to that of detection of ovulation in humans. Whereas human women change temperature during their cycle, they exhibit similar temperatures from cycle to cycle. This is not the case in cattle. The reason for recording temperatures presented in GB 2077593 is in order to establish a temperature baseline for a single animal for a single cycle from which temperature changes associated with oestrus may be detected. The examples of GB 2077593 show a single reading being taken every day. The temperatures are measured electronically and transmitted by telemetry, but there is no disclosure of computer processing of the data. Presumably the farmer is presented with a set of data for his herd every day and makes his own assessment of them in order to determine which of his cows are in oestrus that day.

EP0424102 discloses a device which provides an indication of temperature and time of ovulation and of predicted periods of fertility. An algorithm for obtaining a steady reading is disclosed which would appear to be similar to that used in standard digital medical thermometers, but there is no disclosure of obtaining multiple temperature readings over an extended period and then discarding those that are spurious and those that are genuine but associated with events irrelevant to ovulation.

Systems and methods described herein may aid in (but are not limited to), the detection of ovulation (or the absence of ovulation) diagnosing infertility or subfertility; the prediction of ovulation as an aid to determining time periods of fertility in order to increase or decrease chances of conception; and the monitoring of medical interventions intended to assist conception in order to improve their success rates and/or reduce the risks of unwanted side effects.

BRIEF DESCRIPTION

Embodiments may provide a method of providing information relevant to the fertility of a female mammal comprising the steps of:

1) taking multiple temperature readings from the female mammal during an extended time period;

2) identifying and disregarding temperature readings having one or more characteristics of irrelevant or faulty data;

3) obtaining one or several representative temperature values for the extended time period;

4) repeating steps 1) to 3) over multiple extended periods;

5) analysing the representative temperature values obtained over multiple extended periods in order to identify a pattern in the representative temperature values indicative or predictive of ovulation in order to provide information relevant to the fertility of the female mammal to a user.

There is also described herein use of a method as an aid to diagnosis of anovulation or the diagnosis of irregular ovulation or as an aid to the diagnosis of subfertility or infertility or an aid to conception (including as an aid to assisted conception), or as a contraceptive method.

There is also described herein a device for providing information relevant to the fertility of a female mammal comprising:

a temperature measuring device far taking multiple body temperature readings from the female mammal during multiple extended periods;

a memory for storing said temperature readings;

a processor for identifying temperature readings having one or more characteristics of irrelevant or faulty data and either deleting said readings or labelling them to be subsequently disregarded; and for obtaining one or several representative temperature values for each extended period; and for analysing the representative temperature values obtained over multiple extended periods for one or more patterns in the representative temperature values indicative or predictive of ovulation; and a signalling device to provide information relevant to the fertility of the female mammal to a user.

There is also described a user terminal comprising:

a temperature measuring device for taking multiple body temperature readings from a female mammal during multiple extended periods;

a memory for storing said temperature readings;

a means for communicating the multiple body temperature readings or a derivative thereof, stored in the memory to a remote data processing device;

a means for receiving information relevant to the fertility of the female mammal from a remote computer file server;

a signalling device to provide said information relevant to the fertility of the female mammal to a user.

There is also described a remote data processing device comprising:

means for receiving multiple body temperature readings of a female animal or a derivative thereof from a user terminal;

a processor for identifying temperature readings having one or more characteristics of faulty or irrelevant data and either deleting said readings or labelling them to be subsequently disregarded; and for obtaining one or several representative temperature values for each extended period; and for analysing the representative temperature values obtained over multiple extended periods for one or more patterns in the representative temperature values indicative or predictive of ovulation and thereby provide information relevant to the fertility of the female mammal to a computer file server for later retrieval by a user.

There is also described a remote computer file server holding information relevant to the fertility of multiple female mammals, the information relating to each female mammal being labelled with a unique identifier code corresponding to an individual female mammal, said file server being arranged to provide to a user, the information labelled with a particular unique identifier code in response to the provision of that code to the remote computer file server.

Figure 1:
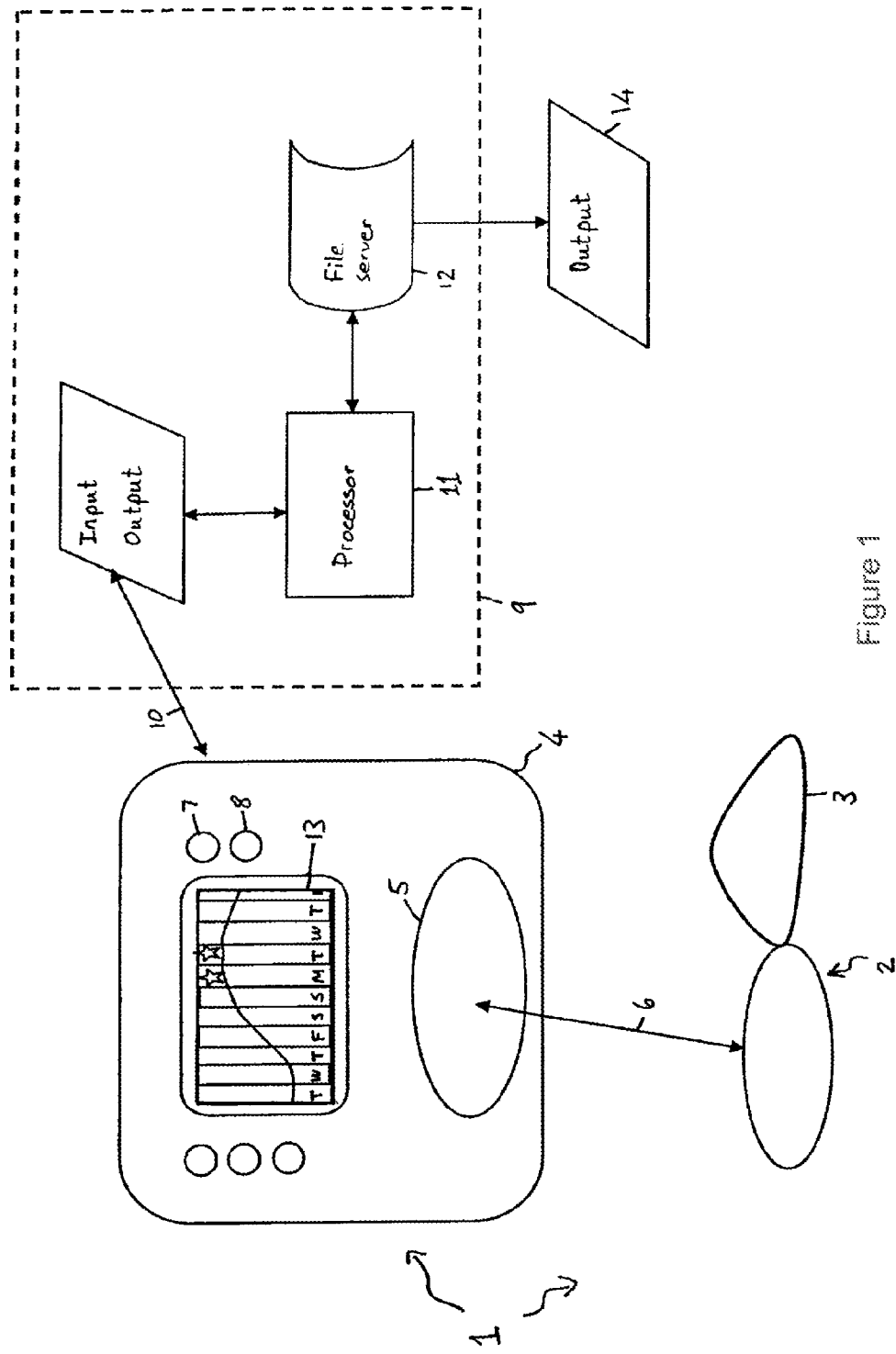
FIG. 1 illustrates a device and its use according to one embodiment of the invention.

The short gaps between the overnight temperatures represent the daytime period during which temperature readings were not taken.

DETAILED DESCRIPTION

There is described herein a method of providing information relevant to the fertility of a female mammal comprising the steps of:

i) taking multiple temperature readings from the female mammal during an extended period;

ii) identifying and disregarding temperature readings having one or more characteristics of faulty or irrelevant data;

iii) obtaining one or several representative temperature values for the extended period;

iv) repeating steps (i) to (iii) over multiple extended periods and over multiple ovulatory cycles;

v) analysing the representative temperature values obtained over multiple extended periods and ovulatory cycles for one or more patterns in the representative temperature values indicative or predictive of ovulation in order to provide information about fertility of the female mammal to a user.

According to certain embodiments, the method may be used to predict ovulation, meaning that the method will indicate that ovulation is imminent. According to other embodiments the method may be used to indicate ovulation meaning that the method will provide an indication to the user at approximately the same time as ovulation takes place.

According to certain embodiments the method may be used to detect ovulation, anovulation or irregular ovulation in order to provide information of relevance to the diagnosis of fertility, subfertility or infertility.

The information relevant to the fertility of the female mammal may be information identifying the timing of ovulation. Such information may include information identifying the timing of ovulation events that have already taken place and/or information predicting the likely timing of future ovulation events.

According to certain embodiments the indication to the user is provided to a computer file server or other archive for later retrieval by a user.

According to certain embodiments the method provides an indication to the user a few days (for example 1 to 6 days or 4 days) before ovulation to give sufficient warning of the fertile time period to allow intercourse to take place before the female cycle reaches the stage where progesterone causes the characteristics of the cervical mucus to change so as to make it impenetrable to sperm. It should be noted in this regard that sperm is able to survive in the female reproductive tract for several days and that sperm may take a few days to swim to the oocyte and so the best time for intercourse (or artificial insemination) so as to ensure maximum fertility will be just prior to ovulation (for example approximately 4 days before).

According to certain preferred embodiments, the method indicates to the user, the start and end times of the next window of fertility.

Taking Multiple Temperature Readings

Embodiments involve taking multiple temperature readings from the female mammal during an extended period. The extended period may be at least 1 hour long, preferably at least 2 hours long, preferably at least 3 hours long, preferably at least 4 hours long. According to certain preferred embodiment that extended period is between 15 minutes and 6 hours, preferably between 1 to 6 hours, more preferably between 2 and 5 hours, more preferably between 3 and 4 hours. According to certain embodiments the extended time period is an overnight time period. One advantage of using an overnight period is that natural fluctuations are reduced due to the constancy of the environment and the relative lack of movement by the female. By "overnight time period" as used above it is intended to mean the period during which the female animal is asleep or expected to be asleep. It will be understood that for certain women (for example those employed to work at night) this time period may in fact take place during the day. Similar considerations apply to the use in nocturnal animals.

During the extended period multiple temperature readings are taken. For example, a reading may be taken every 20 seconds, every minute, or every 5 minutes. Preferably, a reading taken every 1 to 20 minutes, more preferably every 2 to 10 minutes, most preferably every 5 minutes. Preferably multiple temperature readings are taken at regular intervals. Preferably at least 25 temperature readings, more preferably at least 50, more preferable at least 100, more preferably at least 250 temperature readings are taken in the extended period. According to certain embodiments measurements are taken every 5 to 10 minutes over a period of about 5 hours. According to certain preferred embodiments the extended period may extend from shortly before or shortly after the subject goes to bed to 3, 4 or 5 hours later or until the woman wakes up, or for a particular time window during an overnight period, for example, from 1.00 am to 5.00 am or from 12 midnight to 3.00 am. Accordingly, to certain embodiments the time period may be selected to avoid the period after about 3.00 am when a dip in temperature typically occurs, although the Inventors do not report problems with taking readings during this dip.

Identifying Faulty or Irrelevant Data

The method described has as its second step the identification and disregarding of temperature readings having one or more characteristics of irrelevant or faulty data.

There is a difference between faulty data and irrelevant, that is to say data which is genuine but which is irrelevant to ovulatory cycle. Faulty data is data that does not genuinely correspond to the body temperature of the female. If may be produced, for example, by, a faulty temperature measuring device or, more likely, by an intrinsic limitation of the temperature measuring device (for example a time-lag in the response of the device to being placed in a body cavity). Irrelevant data is genuine data because it genuinely reflects the body temperature of the female. However, it is caused by factors that are irrelevant to the matter of ovulation. It may be produced, for example, by diurnal temperature fluctuations, or by changes in the ambient temperature to which the woman is exposed.

Irrelevant or faulty data may arise from a number of sources. For example, data from time period during which the user is experiencing an episode of fever. Also, an indwelling thermometer may be removed or repositioned if it is uncomfortable; it may be removed and washed in either hot or cold water; its temperature may change if the female urinates or if body temperature changes due to changes in the external temperature (caused by changing weather or room heating); changes in clothing or bedding; changes in level of exertion or changes in proximity to external heat sources (for example a hot water bottle or bed partner).

Faulty data is also likely to be generated when the temperature measuring device is first applied to or placed in the subject because of the thermal lag time required for the device to reach body temperature. Irrelevant data may also be produced when the temperature measuring device is not applied to or placed in the subject (for example during periods of non-use which may be intentional or accidental).

A method which allows irrelevant data generated when the device is not in use to be disregarded may have the additional advantage of allowing automatic sensing of the start and end of the extended measuring period. For example if the method involves the overnight use of an indwelling temperature measuring device, said device being stored at room temperature during the day, a step of disregarding irrelevant data will permit the temperature readings generated during the day to be disregarded and assist in the identification of separate extended periods each corresponding to an overnight period. This will remove the need for manually "switching on" the device each night. Faulty or irrelevant data may be identified by applying any suitable characteristic known to be associated with faulty or irrelevant data. Such characteristics include:

1. Temperature readings clearly out of the temperature range found in female mammals of the species in question, for example temperature readings above or below that expected of a female mammal of a particular species. For example more than 2 or 3 or 4 degrees Celsius above or below the expected body temperature of the mammal, for example in the human more than 38° C. or less than 36° C.
2. Temperature readings that whilst they may be within the range expected from female mammals of the species in question are not within the range expected for the individual in question (as determined from historical data previously obtained from that individual, for example temperature readings above or below that expected of an individual female mammal. For example more than 0.5, 0.6, 0.7, 0.8, 0.9 or 1, 2 or 3 or 4 degrees Celsius above or below the expected body temperature of the individual female mammal.
3. Temperature readings which differ from preceding or following values by such a degree as to indicate changes of temperature (heating or cooling) at a rate too high to be expected to be observed in the body temperature of a female mammal. For example heating or cooling rates of more than 0.1° C. per minute, of more than 0.2° C. per minute, of more than 0.3° C. per minute, of more than 0.4° C. per minute, or more than 0.5° C. per minute, or more than 0.6° C. per minute, of more than 0.7° C. per minute, of more than 0.8° C. per minute or of more than 0.9° C. per minute or of more than 1.0° C. per minute may be characteristic of faulty or irrelevant data.
4. Temperature readings which are clearly outliers may be characteristic of faulty or irrelevant data. For example a single reading or relatively few temperature readings differing substantially from the other temperature readings collected during the extended period are unlikely to indicate a true change in temperature but are more likely to be indicative of faulty or irrelevant data.
5. Temperature readings tagged with supplementary data, for example readings tagged by data indicating that the female was suffering from a fever.
6. Temperature readings obtained immediately before or immediately after temperature readings showing any other characteristic of faulty data. For example readings of below 36° C. may be identified as faulty or irrelevant according to characteristic 1 above. The readings obtained 20 minutes before and 20 minutes after such a reading may also be identified as faulty or irrelevant.

Temperature readings having one or more characteristics of faulty data are disregarded, meaning that they are not included in subsequent steps of the method.

Readings which are significantly influenced by diurnal temperature changes may be characteristic of irrelevant data and may, according to certain embodiments be disregarded. For example, if the temperature readings are taken in a human woman during overnight extended periods, the temporary core temperature dip which occurs in humans just before waking may be disregarded according to certain embodiments. Diurnal temperature changes which are unconnected to levels of female hormones and therefore unrelated to ovulation may also be observed in male mammals. Therefore temperature readings taken from female mammals that show similar characteristics to those observed in males of the same species may, optionally be regarded as characteristic of faulty or irrelevant data and be disregarded.

Readings which are identified as raised due to illness by pattern recognition algorithms may be recognised as having one or more characteristics of faulty or irrelevant data and be disregarded.

Readings which occur with the commencement of use, or at the end of use, of the device and which may be attributed to the device reaching a new thermal equilibrium may be recognised as having one or more characteristics of faulty or irrelevant data and be disregarded.

Obtaining One or Several Representative Temperatures Values for the Extended Period In order to compare and analyse temperature readings obtained from different extended periods, it is necessary to obtain one or several representative temperature values for each extended period or to obtain a comparative measurement between selected measurements within extended periods. For example, a comparison is made between single measurement points matched in time from within two or within several extended periods. According to certain preferred embodiments a single representative value is obtained for each extended period. According to other embodiments several representative temperature values are obtained for each extended period. An extended period typically lasts for several hours. Representative temperature values may, for example, be obtained for each hourly or half hourly interval of the extended period.

Preferably within each 24 hour period there is a single extended period of a single representative temperature value is obtained for each extended period. Representative temperature values may, for example, be obtained by any of the following steps:

Calculating the mean of the non-disregarded temperature readings collected during the complete extended period or collected during a specific time interval of the extended period (if more than one representative value is to be obtained for each extended period).

Calculating the median of the non-disregarded temperature readings collected during the complete extended period or collected during a specific time interval of the extended period (if more than one representative value is to be obtained for each extended period).

Calculating the mode (most commonly occurring temperature reading) from the data collected during the complete extended period or collected during a specific time interval of the extended period (if more than one representative value is obtained for each extended period).

Choosing the temperature reading or readings at a particular distance in time from the start or the end of a stretch of non-disregarded temperature readings. For example, the representative value may be chosen as the temperature reading taken halfway through the stretch of non-disregarded temperature readings. Alternatively representative values may be chosen as the temperature readings taken at regular intervals during a stretch of non-disregarded temperature readings, for example, every hour or every half hour.

By the use of deviations of single measurement points from a representative or from an idealised model of diurnal temperature change, for example by calculating a standard deviation, a variance or higher moments.

Calculating a derivative or integral of the temperature readings over time collected during the complete extended period or collected during a specific time interval of the extended period (if more than one representative value is to be obtained for each extended period). For example, the slope representing the rate of change of temperature.

According to certain preferred embodiments, all temperature readings that remain after those having one or more characteristics of faulty or irrelevant data are disregarded are used as representative temperature values.

It has been unexpectedly discovered by the Inventors that contrary to the teaching of DE3342251 which suggests that maximum or minimum temperature readings for each extended period make good representative temperature values, it is preferable to obtain a representative temperature value that is not influenced, or not significantly influenced, by the maximum or minimum readings for extended period. Examples of such values include the "trimmed mean" of the temperature readings. To obtain such a trimmed mean one disregards a pre-determined number of the lowest and a pre-determined number of the highest readings obtained during an extended period and calculates the mean of those readings that remain. Median and mid-percentile (for example 10th to 90th or the 20th to 80th percentile or the 30th to 70th percentile values are also relatively immune to the effects of other temperature readings and are preferred in accordance with certain embodiments of the invention.

A further surprising discovery of the Inventors is that irrelevant temperature readings are more likely to come about because of heating of the female subject than by cooling of the subject (i.e., a woman's temperature during an overnight (asleep) extended period is more likely to deviate from her true basal body temperature in an upward rather than downward direction). That is to say, a woman is more likely to experience a temporary and irrelevant temperature rise than she is a temporary and irrelevant temperature fail. The reason for this is not fully understood but it is reliably observable in most women and is therefore assumed to be a factor of an underlying and universal physiological phenomenon.

This observation means that a better representative temperature value may be obtained for an extended period by use of an algorithm that gives greater statistical weighing to temperature readings that are lower than the median temperature reading than is given to the temperature readings that are higher than the median temperature readings (whilst, of course, at the same time giving little weight to the minimum temperature reading and those reading near to the maximum temperature reading).

It has been found that the 25th percentile of non-disregarded temperature reading makes an especially good representative temperature value for an extended period. Other readings near to the 25th percentile of non-disregarded temperature readings will also serve well. According to certain preferred embodiments the representative temperature value for an extended period is the 10th to 60th percentile value of the non-disregarded temperature readings. More preferably it is the 11th to 50th percentile value, more preferably the 12th to 40th percentile value, more preferably the 13th to 46th percentile value, more preferably the 14th to 44th percentile value, more preferably the 14th to 42nd percentile value, more preferably the 15th to 40th percentile value, more preferably the 16th to 38th percentile value, more preferably the 17th to 37th percentile value, more preferably the 18th to 35th percentile value, more preferably the 19th to 33rd percentile value, more preferably the 20th to 31st percentile value, more preferably the 21st to 29th percentile value, more preferably the 22nd to 28th percentile value, more preferably the 23rd to 27th percentile value, more preferably the 24th to 26th percentile value. Most preferably it is the 25th percentile value.

Step ii and iii of the Method Carried Out Together

It will be appreciated that under some circumstances the temperature readings may be subjected to processing which will result in both the disregarding of faulty and irrelevant data and the obtaining of a representative temperature value. In those circumstances one may regard steps ii and iii of the method of the invention as taking place simultaneously. For example, if one were to take the raw temperature readings of an extended time period and calculate a trimmed mean one would be disregarding outlying temperature readings (likely to be faulty or irrelevant data) and obtaining a representative temperature value in a single step. Although both steps may take place simultaneously it should be appreciated that both ii), identifying and disregarding temperature readings having one or more characteristics of faulty or irrelevant data, and iii), obtaining one or several representative temperature values for the extended period, need to take place in accordance with a method of the invention.

Repeating Over Multiple Extended Periods

The steps of taking multiple temperature readings over an extended period, disregarding temperature readings having the characteristics of faulty or irrelevant data and obtaining one or several representative temperature values for each extended period, are repeated over multiple extended periods.

Preferably said steps are repeated over at least 2, 3, 4, 5, 6, 7, 8, 9, 10, 11, 12, 13, 14, 15, 16, 17, 18, 19, 20, 21, 22, 23, 24, 25 or 26 extended periods (in general the larger number of extended period the more preferred). Most preferably said steps are repeated over multiple extended periods covering several days (preferably with one extended period each day). Preferably said steps are repeated over at least one fall ovulatory cycle, more preferably over several cycles.

Preferably said steps are repeated over a sufficient number of extended periods such that said extended periods would be expected to extend over a time period sufficient for one (or preferably more than one) ovulatory cycles to take place in an archetypical fertile female mammal of the species of interest regardless of the fact that the individual female mammal from which the temperature readings are taken may or may not have ovulatory cycles. Preferably said steps are repeated over a sufficient number of extended periods such that there is at least one extended period in most of the days of an ovulatory cycle. For reasons of comfort and hygiene it is not appropriate for an intravaginal indwelling device to be worn during days of menstruation. In such circumstances it is preferable for there to be at least one extended period (preferably a single extended period) corresponding to each and every day of the ovulatory cycle in which menstruation does not take place.

Analysis of Representative Temperature Values

The fifth step of the method comprises analysing the representative temperature values obtained over multiple extended periods for one or more patterns in the representative temperature values indicative or predictive of ovulation. By "analysis for one or more patterns indicative or predictive of ovulation", it is meant that the analysis is such that should ovulation have taken place or be imminent, the analysis will identify one or more patterns indicative or predictive of ovulation. If ovulation has not taken place and is not imminent such patterns will not be identified.

According to certain embodiments, it is preferred that the multiple extended periods for which representative temperature values are analysed comprise at least 3 extended periods, more preferably at least 5 extended periods, more preferably at least 7 extended periods, more preferably at least 9 extended periods, more preferably at least 12 extended periods, more preferably at least 14 extended periods, more preferably at least 16 extended periods, more preferably at least 18 extended periods, more preferably at least 20 extended periods, more preferably at least 22 extended periods, more preferably at least 24 extended periods, more preferably at least 26 extended periods, most preferably 28 or more extended periods.

According to certain preferred embodiments wherein each extended period corresponds to an overnight period during which temperature readings are taken, the multiple extended periods for which the representative temperature values are analysed correspond to and equal in number all of the days of a complete cycle minus the days during which menstruation takes place.

Preferably said multiple extended periods comprise those collected over at least one, preferably several ovulatory cycles. According to certain preferred embodiments said multiple extended periods extend over every day of one or more ovulatory cycles with the exception of those days in which menstruation takes place, when useful temperature data is unlikely to be collected and the use of an indwelling temperature recording device may be undesirable for reasons of comfort and hygiene.

According to certain preferred embodiments said analysis occurs in real time, that is to say, as soon as temperature readings are obtained for an extended period, one or more representative temperature values are obtained and are subjected to analysis in comparison with previously obtained representative values so that any outcome of the analysis may be signalled in the next step of the method without necessarily requiring all of the representative values to necessarily have been obtained.

However, according to other preferred embodiments the temperature readings are collected for a whole menstrual cycle (or for a whole menstrual cycle with the exception of days wherein the obtaining of temperature readings either by accident or intention did not take place) and stored. On completion of that cycle (signalled by the onset of menses) the temperature readings processed to give representative values and analysis of the cycle that has just finished is undertaken.

Analysis of the representative temperature values involves the identification of a pattern in the representative temperature values indicative or predictive of ovulation only if such a pattern is present in the representative temperature values. In an anovulatory woman, analysis will involve seeking but not finding such patterns.

Patterns in representative temperature values indicative or predictive of ovulation include the peak in body temperature associated with the LH peak which occurs just before ovulation and the earlier temperature dip associated with the rise in oestradiol.

Because the temperature dip associated with the rise in oestradiol occurs earlier and the period of peak fertility in humans is several days before ovulation, it is preferred that the method of the invention detects the oestradiol-associated temperature dip. The Applicant is not aware of any prior art removable device that is able to accurately detect this temperature dip because its magnitude is small. The device of the present invention in its preferred embodiments is able to reliably detect the oestradiol-associated temperature dip because of its high accuracy in temperature measurement and innovative data processing (for example the disregarding of faulty and irrelevant data).

For example, methods of pattern identification which may be used are already described in the literature. See for example McCarthy et al (1983) A comparison of methods to interpret the basal body temperature graph. *Fertility Sterility* 41 640-646. For example the "three over six" method in which ovulation is indicated when three consecutive representative temperature values are registered, all of which are above the average of the representative temperature values of the last six proceeding days. Ovulation is deemed to have occurred on the day preceding the first day of the 3 consecutive days showing elevated representative temperature values. According to the usual application of this rule a single day corresponds to a single representative temperature value.

Similar, but more sophisticated methods may also be employed. These are essentially, as are the above methods, based on statistical quality control and process control methods and these are described in, for example, Ryan, T. P. (1989) Statistical Methods for Quality Improvement John Wiley & Sons, New York; Wetherill, G. B. and Brown, D. W. (1991) Statistical Process Control. Chapman and Hall, New York.

For many women the "3 over 6" rule gives a satisfactorily robust determination of the day of ovulation.

However, it has a drawback in that it requires temperature values to have been obtained on each of the 6 days prior to ovulation. This may not have been achieved in practice because of a very short or irregular cycle or because of obtaining temperature readings in all 6 days may have been missed.

It is therefore proposed to use in certain preferred embodiments an alternative to the "3 over 6" rule which can either be used in place of the "3 over 6" rule or as a fall-back analysis method for use when the "3 over 6 rule" fails to detect on ovulation. Again according to the usual application of this rule, a single representative temperature value is obtained per day.

According to this alternative rule the mean of at least three consecutive representative temperature values is obtained and compared with the following 3 representative consecutive representative temperature values. If the following 3 consecutive temperature values are higher than the mean, ovulation is deemed to have taken place on the corresponding to the first representative temperature value. If not, the analysis is repeated but this time the mean is obtained from 4 consecutive representative temperature values. If ovulation is not detected the analysis is repeated again but this time the mean is obtained from 5 consecutive temperature values, then from 6, 7, 8, 9, 10, etc until ovulation is detected or the end of the cycle is reached.

In either the "3 over 6" rule or the improved version described above in order for ovulation to be deemed to have occurred the 3 consecutive representative temperature values should be higher than the mean (either the mean of the 6 proceeding values as in the "3 over 6" rule or the "cumulative mean" in the improved rule described above) by more than a pre-set threshold amount. That threshold amount should be set at a value which provides for reliable detection of genuine ovulations with the minimum of false positives. Preferably the threshold value is from 0.08 to 0.25° C., more preferably from 0.09 to 0.24° C., more preferably from 0.10 to 0.23° C., more preferably from 0.11 to 0.22° C., more preferably from 0.12 to 0.21° C., more preferably from 0.13 to 0.20° C., more preferably from 0.14 to 0.18° C., more preferably from 0.15 to 0.17° C., more preferably from 0.16 to 0.17° C., most preferably 0.1667° C. If, according to the this method, more than one apparent ovulation is detected, further analysis may be used to decide which apparent ovulation is most likely to correspond to the true ovulation. Either the analysis of the representative temperature value may be repeated with an incrementally increased pre-set threshold value (as explained above) until only a single apparent ovulation event is detected, or the timing of the multiple apparent ovulation events is considered and the event occurring nearest to the expected day of ovulation (calculated from data obtained from prior cycles—or if not available from population averages) is chosen as the day of true ovulation.

Preferably, the method used may be further enhanced by using historical data and a Bayesian approach to evaluation or to prediction. 'Prior' (historical) data can be provided either from population data available in the literature or from data available from previously recorded cycle/s for the individual female mammal or preferably from both population data and from the individual female's previous cycle or cycles. For example, data such as the 'corrected day—specific probabilities of clinical pregnancy' as provided in Dunson et al (2001) Assessing human fertility using several markers of ovulation. *Statistics in Medicine* 20 965-978 can be used to enhance the evaluative or the predictive method in human females. The 'prior' data are combined with the current data using a Bayesian methodology to enhance evaluation or prediction.

Input of Supplementary Information By User

In addition to data deriving from the recorded temperature readings, according to certain embodiments the analysis of representative temperature values may also involve the use of supplementary information inputted by the user.

For example, the user may be required to identify the first day of her cycle (first day of menses) by pressing a button on the device or by entering the date prior to the analysis step of the method. That information may be used to identify cycle length and to place detected ovulation into the context of the full cycle.

Additionally it is known that fever caused by infection may affect basal body temperature. The method of the invention therefore optionally provides the facility for such days to be tagged or otherwise be identified by the user and excluded from subsequent analysis.

Dealing with Missing Data

On occasions, a representative temperature value may not have been available for a particular extended period. This may be the case if no temperature readings have been obtained for that extended period or if the user has requested that the value for that extended period be discounted (by, for example, identifying that extended period as having taken place during a period of fever).

Appropriate statistical methods may be used to minimise the impact of missing data.

For example, if the day of ovulation as detected by an elevated basal body temperature is determined to take place on a day after a day for which data is missing, the ovulation may in fact have taken place on either of the two days. The method of the invention may therefore include the step of deciding on which day ovulation was most likely to have taken place. This decision may involve deciding which day is most likely the day of ovulation by comparison with prior data from previous cycles (or such data is not available population average data).

Provision of Information to User

The final part of the method described comprises providing information relevant to the fertility of the female mammal to a user.

In its simplest form that information may be provided visually (i.e., by the illumination of a lamp or LED or the display of graphical information on an LCD). If the user is a female human the information may be provided directly to her. Alternatively or additionally, the information may be provided to a person responsible for the medical or veterinary supervision of the female animal. For example information may be provided to a woman's physician or to a veterinary surgeon. Such a provision of information may involve the electronic transmission of a signal, for example via the internet, via a wireless radio network (for example an SMS or "text" message) or via a telephone line.

According to certain embodiments, the information may be supplied to multiple people. If the method is used by a human couple in order to assist in timing intercourse so as to maximise the chance of conception, a signal indicating immediate or imminent fertility could be sent to both partners by text message to enable them to plan their intercourse.

If the method is used as an aid to medical diagnosis it may not be appropriate to indicate the signal directly to the patient because of the possibility for misinterpretation (especially misinterpretation in the absence of other medical results) and the causing of unnecessary anxiety and distress. Instead the signal may be communicated to the patient's physician for medical evaluation (typically involving the factoring in of other information, for example the results of blood tests) before a diagnosis is reached and communicated to the patient.

According to certain embodiments, the information need not be directly communicated to the user. Instead it may be sent electronically to a data store (for example a remote computer file server) where it may be retrieved at a later date either by the patient or by their medical supervisor.

According to certain embodiments, the information is immediately communicated to a female human and a further signal is sent to that female human's electronic medical records to be retrieved in the future if and when required.

According to certain embodiments simplified information may be supplied to the woman (for example the message "your cycle lengths are irregular, you should discuss this with your doctor") and more detailed data supplied to the woman's doctor (including under some circumstances raw temperature readings or details of the representative temperature values for each extended period).

According to certain preferred embodiments, the information communicated to the user includes a predicted start date and predicted end date of the next "fertility window" (i.e., period during which insemination has a relatively high chance of resulting in a pregnancy). The method of the invention may be used for the detection of ovulation as an aid to diagnosis of subfertility or infertility, for example, by the identification of patients in which ovulation is absent or irregularly timed. The diagnosis of a disorder of ovulation may allow an appropriate surgical or drug treatment to be offered and the success or otherwise of treatment aimed at bringing about ovulation can be monitored. The method of the invention also assists in determining the best timing for IUI (Intrauterine Insemination) or IVF (in vitro fertilisation).

Alternatively, detection of some types of subfertility may lead to the recommendation that further monitoring of ovulation take place according to the invention as an aid to conception.

Information relevant to the fertility of a female mammal provided by the remote computer file server to a user may include a specific alert that one or more of the following events have taken place:

(1) Female about to enter a predicted fertile period.
(2) Female has just ovulated (i.e. LH peak associated with temperature rise detected).
(3) Patient failed to ovulate within more than 1, more than 2, more than 3, more than 4, more than 5, more than 6, more than 7, more than 8, more than 9 or more than 10 days of predicted ovulation date.
(4) An anovulatory cycle completed.
(5) Cycle more than 1, more than 2, more than 3, more than 4, more than 5, more than 6, more than 7, more than 8, more than 9, or more than 10 days different in length from previous cycle.
(6) Monophasic cycle detected (i.e. no pre-ovulation LH peak detected, possibly indicative of low oestrogen output).
(7) An abnormal length of cycle. For example a cycle length outwith the 2.5 and 97.5 percentiles expected for the species, i.e. more than 37 days or less than 20 days.
(8) A post-ovulatory phase (i.e. number of days following detection of ovulation to start of next cycle of less than 9 days).

If the user is a female woman for whom fertility information is being provided, the information provided may be limited to information about predicted fertility at a future time (i.e. item 1 on the above list). Items 2 to 8 are useful for diagnostic purposes and so may more usefully be provided to a user who is a physician responsible for the care of the female woman for whom fertility information is being provided. Items 3 to 8 are events associated with infertility and subfertility. However, women with "normal" fertility may occasionally experience some of these events. It may therefore be appropriate to provide information to a user if events 3 to 8 occur a sufficient number of times to indicate a fertility problem, for example, if they occur more than twice in any three consecutive cycles.

Alternatively, the method may be used for the detection of ovulation as an aid to the prediction of fertility at any particular instant in time, such information being of use both as an aid to conception and as a method of contraception. In such circumstances it may be preferable that the signal provided to the user is a simple binary indication of "fertile" (ovulation detected or predicted as imminent) or "non-fertile" (ovulation not detected or imminent). When the method is used as an aid to conception copulation (or artificial insemination) can be timed to take place when a "fertile" indication is given. When the method is used as a form of contraception, unprotected sex can take place when a "non-fertile" indication is given. A "fertile" indication informs the user to either abstain from sex or to use a supplementary form of contraception (for example a method of barrier contraception such as a condom).

Prediction of Fertile Period

The oestodial-associated temperature dip proceeds ovulation by approximately 4 days. The detection of this dip may therefore be used to identify the start of the "window of fertility".

However, for methods based on the detection of temperature rises associated with the LH-surge, the temperature rise is detected at the end of the "window of fertility". The detection of the LH-surge therefore comes too late to inform the user of the timing of the fertility window in the current cycle. It can, however, be used to determine the day of ovulation which can be used to predict the window of fertility in the next cycle.

According to such methods, the day of ovulation in the current cycle is determined. At the start of the next cycle the day of ovulation is predicted used on the day of ovulation (i.e., the number of days since the start of the cycle) observed in previous cycles (for example the day of ovulation may be estimated to take place on the median of the day it took place on up to the 12 previous cycles. If information on the previous days of ovulation is not known (which would be the case if the user had only recently started to use the method, then population average data may be used until better data is available.

Once a future day of ovulation is known, the "window of fertility" may be calculated based on the assumption that it begins 5 days before ovulation and ends 1 day after ovulation.

Use in Monitoring Methods of Assisted Conception

Several methods of assisted conception involve the administration of drugs that cause super-ovulation. Such methods carry a risk that multiple fertilisations will take place and multiple pregnancies result. In order to minimise that risk it is useful to know how many ova have been released during a particular ovulation event. The number of ova subsequently released correlates with the magnitude of the pre-ovulating oestradiol surge and therefore with the pre-ovulating temperature dip.

According to certain embodiments, the pre-ovulating oestrodiol-associated temperature dip may be observed and its magnitude analysed to give an indication of the number of ova that may have been released. If a large number of ova appear to have been released the risk of multiple pregnancies will be elevated and it may be decided to abandon attempted fertilisation (for example fertilisation by natural methods or by IUI) in the current cycle.

There is also described a device for providing information relevant to the fertility of a female mammal comprising:

A temperature measuring device for taking multiple body temperature readings from the female mammal during multiple extended periods;
A memory for storing said temperature readings;
a processor for identifying temperature readings having the characteristics of irrelevant or faulty data and either deleting said readings having the characteristics of faulty or irrelevant data or labelling them to be subsequently disregarded; and for obtaining one or several representative temperature values for each extended period, and for analysing the representative temperature values obtained over multiple extended periods for one or more patterns in the representative temperature values indicative or predictive of ovulation; and
a signalling device to provide information relevant to the fertility of the female mammal to a user.

Particular features identified as optional or preferred in respect of the foregoing description of the method of the invention (for example details of the signalling device, the information, the extended periods, the recordal of temperature readings, the characteristics of faulty or irrelevant data, the representative temperature values, the analysis of representative temperature values and the patterns indicative or predictive of ovulation) are also optional or preferred in respect of the device of the invention.

The temperature measuring device is preferably an indwelling device which is preferably introduced into the vagina of the female mammal and left to dwell for a period of time, for example a week, a month or an overnight period or for several days or for an entire menstrual cycle (preferable with the exception of the time of menstruation), and to record the temperature of the female mammal at regular intervals over that period.

When used in the human female the device is preferably smoothly shaped for hygiene and comfort and similarly sized and shaped to a tampon. A suitable cord may be attached to the device for ease of retrieval.

The device for indicating or predicting ovulation in a female mammal according to the invention also comprises a signalling device. Although the signalling device may be provided in the same indwelling unit as the temperature measuring device it is preferably housed in a separate unit (preferably a tabletop or bedside unit).

Communication between two units may require one unit to be electrically plugged into the other. Preferably this is avoided. Communication may be by a wireless radio link. Most preferably communication between the two units will be achieved by placing the indwelling unit onto or very close to the tabletop unit so that communication may take place via the mutual proximity of induction coils in each unit.

If the indwelling unit is to be left in the female mammal overnight, it is preferably to be placed on the tabletop unit during the day. The tabletop unit may be suitable shaped to retain the indwelling unit placed onto it. For example, the table top unit may comprise a recess to receive the indwelling unit. Features may be provided on the indwelling unit to assist its orientation on the table top unit. For example, shape-features and/or visual markings may be provided to ensure that the relative alignment of induction coils is such that communication between the two units may be optimised.

The indwelling unit is preferably battery (for example, rechargeable battery) powered. The tabletop unit may also be battery powered but may conveniently be powered by mains electricity. According to a preferred embodiment, the two units communicate via proximal induction coils. Said coils may also be used to recharge the battery in the indwelling unit from the mains power provided to the desk top unit. According to certain preferred embodiments the tabletop unit is powered by a rechargeable battery. This allows it to be kept in the bathroom where mains power is generally not permitted. The unit can be recharged in another part of the house during days of menstruation when the product is not in use.

According to certain embodiments the indwelling unit may be disposable after a period of use (for example after use for a set number of cycles or for a set number of days (for example 120 or 150 days).

The device comprises memory for storing the temperature readings.

In the two unit arrangement described above the memory may be provided in either unit. Preferably, the indwelling unit has sufficient memory to store the temperature readings made during an extended period. This stored data is transmitted to the tabletop unit which also has a memory to review said data.

According to alternative embodiments the indwelling unit does not comprise memory and temperature readings are transmitted to the other unit as soon as they are taken (for example by radio waves).

According to certain embodiments the indwelling unit comprises sufficient memory to record the temperature readings for a complete cycle (or for several cycles). The readings need not be transmitted to the table top unit until the end of the cycle.

The device comprises a processor. In the two unit arrangement described above the processor is preferably placed in the tabletop unit. The device according to the invention also comprises a signalling device. In the simplest form this device may be a light (for example an LED). In the two unit arrangement described above, the signalling device is preferably provided on the tabletop unit. According to certain preferred embodiments, the signalling device is a LCD display provided on the tabletop unit.

According to certain preferred embodiments, the signalling device provides information to a female human which includes the predicted start and end times of her next window of fertility. She may also be provided with a simplified summary of her likely fertility and messages recommending visits to her physician when appropriate.

The signalling device may, in the case of a device for use by a female human, provide information to the female human. Alternatively, or additionally the signalling device may provide a signal to the female's physician or to another person.

Whilst the method described herein may be carried out by the device of the invention, it is also provided that the temperature readings and/or the representative temperature values may be sent to a remote processing device for analysis. The result of the analysis may then be sent back to the user in the form of information about fertility of the female mammal or stored on a computer server for access by authorized and authenticated users, which may include the female and/or her medical supervisors).

According to certain preferred embodiments there is described a method wherein one or more of steps:

ii) identifying and disregarding temperature readings having one or more characteristics of faulty or irrelevant data;

iii) obtaining one or several representative temperature values for the extended period;

v) analysing the representative temperature values obtained over multiple extended periods for one or more patterns in the representative temperature values indicative or predictive of ovulation in order to provide information relevant to the fertility of the female mammal to a user are carried out by a remote data processing device.

By remote data processing device it is meant a device remote to the user to which the temperature readings and/or representative temperature values are transmitted by telephony, wireless telephony or by use of an internet protocol.

An advantage of carrying out one or more of steps ii), iii) and v) at a remote data processing device is that the remote data processing device can be shared by multiple users and therefore greater processing power can be provided more cost effectively. Also, software and hardware improvements or upgrades can be provided more conveniently to a central data processing device than to devices located with individual users.

A further advantage of sending the temperature readings and/or temperature values to the remote data processing device is that greater memory capacity can be provided so that the readings or values from one extended period can be more conveniently stored and used in the analysis of representative temperature values obtained from future extended periods. The storage of such data permits a historical picture of the female mammal's temperature readings during a number of previous ovulatory cycles to be built up. That data can be compared with newly obtained data in order to improve the accuracy of the analysis of the newly obtained data.

If the remote data processing device is arranged to be shared by multiple users, it will be sent temperature readings and representative temperature values from multiple users. That data may be stored. Analysis of the representative temperature values obtained from a single female mammal may be analysed by comparing them with the values obtained from other female mammals or by comparing them with derivative data (for example, average data) obtained from other female mammals.

It is known that in humans there is significant variation in their ovulatory cycles between women. By compiling an ever-expanding database of temperature values from multiple women, it will be possible to determine what values may be regarded as normal and what values may be regarded as abnormal. The identification of abnormal values may be a sign of sub-fertility or infertility and therefore an aid to diagnosis of sub-fertility or infertility.

It will be appreciated that there are privacy and data protection concerns raised by the transmittal of medical data to remote data processing devices and by the storage of such data.

It is proposed to address those concerns by allocating unique identifier code to each female mammal. That code will be preferably incorporated into the equipment provided for use by the female mammal. Temperature readings and/or representative temperature values sent to the remote data processing device will be anonymous in that they will not be accompanied by any meaningful identifier of the female (for example name). The unique identifier code means that the female can only be identified by someone who knows which code has been allocated to which female. It may be convenient for the unique code to be both incorporated into the equipment and provided to the female user and/or her physician (for example by being provided on the equipment packaging or in the instruction manual).

The results of the analysis (i.e., the information relevant to the fertility of the female mammal) may be stored on a remote computer server. The female and/or her physician will be the only people who will know her unique identification code. They will be able to use that code to retrieve the data for that female only. Even if they (or someone else) were able to access the data for other women, the privacy of those other women would not be compromised because without knowing the unique identification code for the other women, such data would remain effectively anonymous.

In accordance with certain embodiments of the method of the invention there is provided between step i) and step ii) a further step ia), or between step ii) and step iii) a further step iia), or between step iii) and step iv) a further step iiia).

Said further step ia) comprises labelling the temperature readings with a unique identifier and transmitting them to a remote data processing device, wherein said steps ii) iii) iv) and v) are carried out by the remote data processing device.

Said further step iia) comprises labelling the temperature readings with a unique identifier code and transmitting them to a remote data processing device, wherein said steps iii), iv) and v) are carried out by the remote data processing device.

Said further step iiia) comprises labelling the representative temperature values with a unique identifier code and transmitting them to a remote data processing device, wherein said steps iv) and v) are carried out by the remote data processing device.

Steps carried out prior to step ia) step iia) or step iiia) are carried out by the user's terminal.

According to certain preferred embodiments, the method comprises a further step vi) after step v).

Said step vi) comprises either:

a) transmitting said information relevant to the fertility of the female mammal to the user's terminal or b) storing said information about fertility of the female mammal on a computer server for retrieval by the user's terminal and; optionally by one or more further nominated terminals in possession of the unique identifier code.

In order to carry out certain embodiments of the method, there is also described herein a user terminal comprising:
- a temperature measuring device for taking multiple body temperature readings from a female mammal during multiple extended periods;
- a memory for storing said temperature readings;
- means for communicating the multiple body temperature readings, or a derivative thereof, stored in the memory to a remote data processing device;
- means for receiving information relevant to the fertility of the female mammal from a remote computer file server;
- a signalling device to provide said information relevant to the fertility of the female mammal to a user.

The temperature measuring device, the memory and the signalling device, and their arrangement in one or more units is preferably as described in respect of the device.

There is also described herein a remote data processing device comprising:
- means for receiving multiple body temperature readings of a female animal or a derivative thereof from a user;
- a processor for identifying temperature readings having one or more characteristics of irrelevant or faulty data and either deleting said readings or labelling them to be subsequently disregarded; and for obtaining one or several representative temperature values for each extended period; and for analysing the representative temperature values obtained over multiple extended periods for one or more patterns in the representative temperature values indicative or predictive of ovulation and thereby provide information about fertility of the female mammal to a computer file server for later retrieval by a user.

The multiple body temperature readings, the one or more characteristics of irrelevant or faulty data, the methods of obtaining one or several representative temperature values for each extended; and for analysing the representative temperature values are preferably as described above in reference to the method of the invention.

There is also described herein a remote computer file server holding information about fertility of multiple female mammals, the information relating to each female mammal being labelled with a unique identifier code corresponding to an individual female mammal, said file server being arranged to provide to a user, the information labelled with a particular unique identifier code in response to the provision of that code to the remote computer file server.

According to certain preferred embodiments the remote computer file server is receiving data from a number of female humans who are patients of as specialist fertility physician.

Preferably, the computer file server provides long-term storage of information about fertility of each woman.

Such an arrangement will permit the physician responsible for the care of the woman, and in possession of that woman's unique identifier code, to call up the woman's historical data in numerical and graphical form for review as an aid to diagnosis and/or treatment.

Preferably, the physician is provided with appropriate software to enable said physician to view the data retrieved from the server.

According to certain preferred embodiments, the physician's computer is provided with software that automatically polls the central computer file server, identifies itself and its list of patients, and downloads their data. It then displays to the physician a "highlights list" when she logs on in the morning. Said "highlights list" highlights to the physician information from patients for whom a significant event (for example ovulation) has taken place and or from patients where intervention of the physician may be required. According to certain preferred embodiments, the remote computer file server provides the information on a world wide web page or in the form of e-mails. Such an arrangement removes the need for the physician to have specialist software to view the data retrieved from the server because it could be viewed using a standard web browser or e-mail client software.

The following non-limiting examples illustrate the invention. It is understood that specific technical features disclosed in the context of an example may be generally applied to the invention as a whole:

Example 1

FIG. 1 illustrates diagrammatically an apparatus and method in accordance with a certain preferred embodiment of the invention. It is to be understood that features disclosed in respect of this preferred embodiment may be applied to other embodiments of the invention.

There is provided to a female human a user terminal 1 comprising a temperature measuring device provided in an indwelling unit 2. The indwelling unit 2 is designed for intravaginal use and is smoothly shaped for comfort and hygiene. It is provided with a cord 3 for ease of retrieval. The indwelling device is used worn in the vagina every night from the first night following the end of menstruation until such time as the next menstrual period starts. The indwelling unit comprises an electronic temperature measuring means which takes multiple temperatures readings at regular time intervals during the overnight period. The indwelling unit is powered by battery and comprises a memory unit which records the temperature readings taken during the overnight period. The indwelling unit is waterproof and sealed and therefore is either disposed of when the battery is flat or else is provided with a rechargeable battery and associated circuitry so that it may be recharged.

When the woman wakes up, she removes the indwelling unit and washes it in the bathroom, for example by rinsing under a running tap. During the day whilst the woman is awake and active, the indwelling unit is placed onto a tabletop unit 4 which is also provided to the woman and may be conveniently positioned in the bathroom. The tabletop unit is conveniently provided with a recess 5 in its upper surface which is shaped to retain the indwelling unit placed onto it. Both the indwelling unit and the tabletop unit are provided with induction coils which are arranged so that when the indwelling unit is placed in the recess of the tabletop unit the induction coils come into mutual proximity so that the two units may communicate (illustrated by arrow 6). During the day, the temperature readings stored in the memory of the indwelling unit are transferred to a memory in the tabletop unit. If the indwelling unit is provided with a rechargeable battery, the battery may be recharged by the transfer of electrical energy through the induction coils. At the end of the day the woman removes the indwelling unit from the recess and places it in her vagina so that it may record her body temperatures over the following night.

The indwelling unit is arranged so that it only records temperature readings during an overnight period. Various methods may be employed to ensure that. In one preferred method the indwelling unit will incorporate a clock and will be programmed to record temperature only during a time period when it is expected that the woman would be asleep. In another preferred embodiment, the woman is instructed that with the exception of brief periods of cleaning after removal and before insertion, the device is to be placed in the recess of the tabletop unit at all times when it is not in the vagina. In such an embodiment the indwelling unit will be arranged to sense whether it is in the recess and programmed to take temperature readings only when it is not in close proximity to the table top unit. It may also be programmed to not record or to disregard temperature readings taken within a short time period (for example, 30 minutes) before and after being placed in the recess of the table top device. Such a short time period will likely contain erroneous temperature readings caused by the indwelling unit being washed or by the thermal lag time when it is first inserted and needs to warm up to body temperature. According to another embodiment, the table top unit is provided with user operated buttons (7, 8) which can be used by the woman to instruct the device that she is about to insert the device or that she has just removed the device.

According to certain preferred embodiments the woman is instructed to press a button (either on the indwelling unit or more preferably on the table top unit) to register when she is about to place the indwelling unit and go to bed. Additional input buttons may be provided, for example, for the woman to enter "fever days" to be discounted from calculation or for the woman to signal the start of her cycle (ie the first day of menstruation).

When the table top unit 4 has acquired the temperature readings taken the previous night, those readings are automatically transmitted to a remote site (remote site illustrated by dotted line 9, transmission by arrow 10). Transmission may be by wireless telephony or via a telephone line or via the internet or by any other convenient route for which appropriate hardware (for example, modems) and software protocols are provided.

According to certain embodiments, transmission need not take place until the woman signals the end of her cycle. A whole cycle's worth of readings may then be transmitted. According to such embodiments, a button may be provided on one of the units (preferably the table top unit) for a woman to signal the end of her cycle and also to start the transmission of data relating to the cycle just completed.

At the remote site there is provided a processor 11 for analysing the temperature readings in accordance with the method of the invention, and a file server 12 for storing the temperature readings and the results of the analysis. The remote site may be in communication with multiple tabletop units being used by different women. The readings from each woman are identified by being labelled by the appropriate desktop unit with a unique identifier code.

Information about the fertility of the woman may be transmitted back to that woman's tabletop unit and displayed on a display screen 13 provided on that unit, said information will also be stored, labelled with the woman's unique identifier code, on the file server.

Information relevant to the fertility of the woman may also be accessed from the file server by other authorised users (represented by output box 14) in possession of the appropriate unique identifier code. Such additional users may include the woman's sexual partner and her physician.

Example 2

Day and Night Temperature Readings

Figure 2:
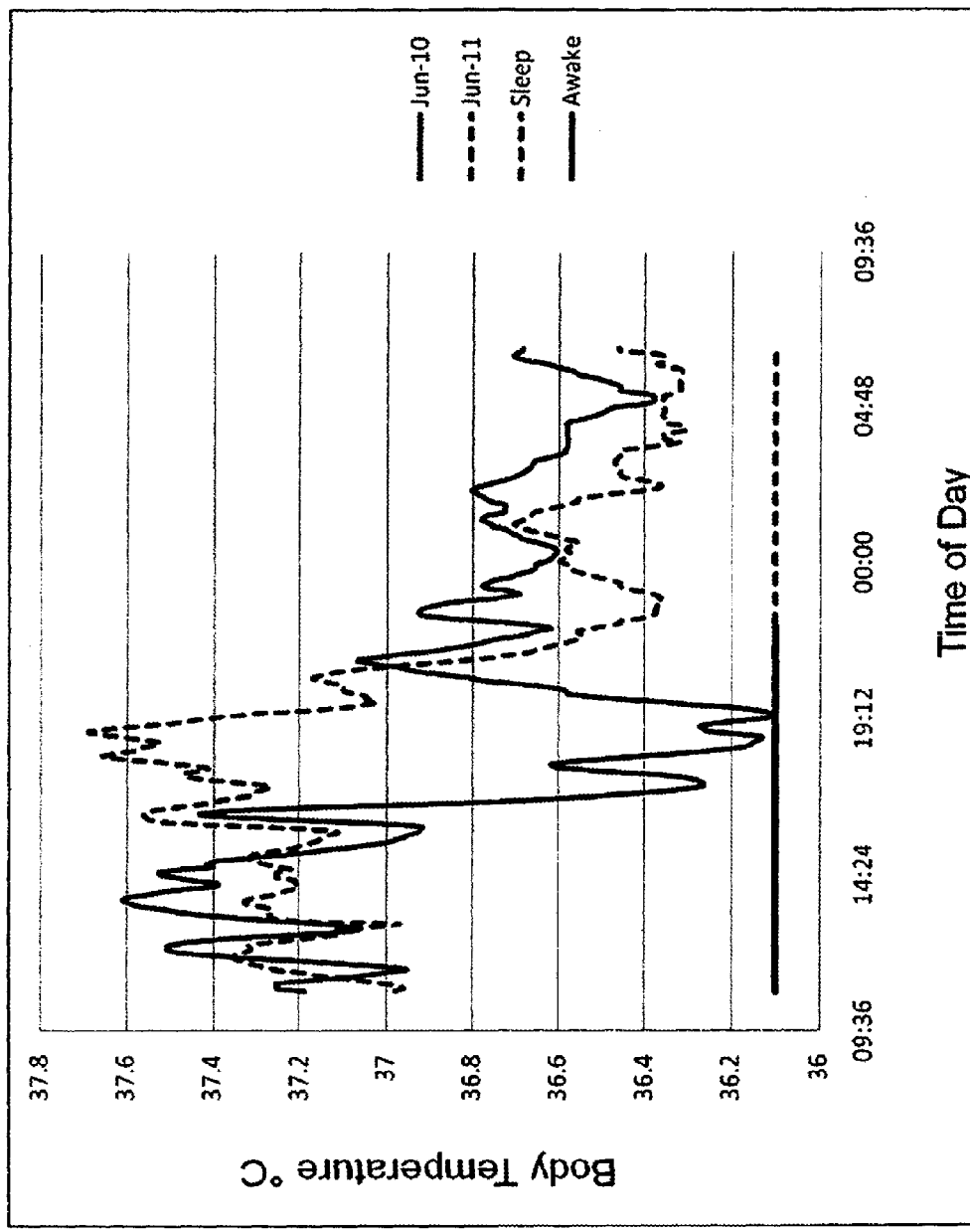
FIG. 2 shows real data obtained from an indwelling thermometer worn by a human female for two consecutive days (10 June as line A and 11 June as line B) The x-axis shows the time of day or night and the bar C below the temperature plots shows when the woman was awake or asleep.

FIG. 2 shows temperature readings taken every five minutes using an intravaginal indwelling temperature measuring device from an individual woman over two consecutive days (10 and 11 June). This 48 hour period encompassed both day time periods when the woman was awake and active and overnight periods when the woman was asleep—the bar at the bottom of the graph shows when the woman was awake and when she was asleep. It can be seen from the graph that the overnight temperature readings when the woman was asleep are subject to fewer fluctuations. This is because they are subject to fewer irrelevant temperature changes. This data suggests that it may be preferable to obtain representative temperature values from temperature readings obtained during an overnight time period when the woman is asleep.

The conclusion drawn from FIG. 2 is reinforced by the data shown in the table below which compares the standard deviation (SD) of temperature readings taken every 5 minutes both during the day and during an overnight time period when the subject was asleep. Data is presented for two different women (subject 1 and subject 2) over two 24-hour periods for each woman.

| Subject | SD of Day Readings | SD of Sleeping Readings |
| --- | --- | --- |
| 1 | 0.266 | 0.112 |
| 1 | 0.453 | 0.122 |
| 2 | 0.286 | 0.088 |
| 2 | 0.289 | 0.111 |

Example 3

Comparison of Alternative Representative Temperature Values

Figure 3:
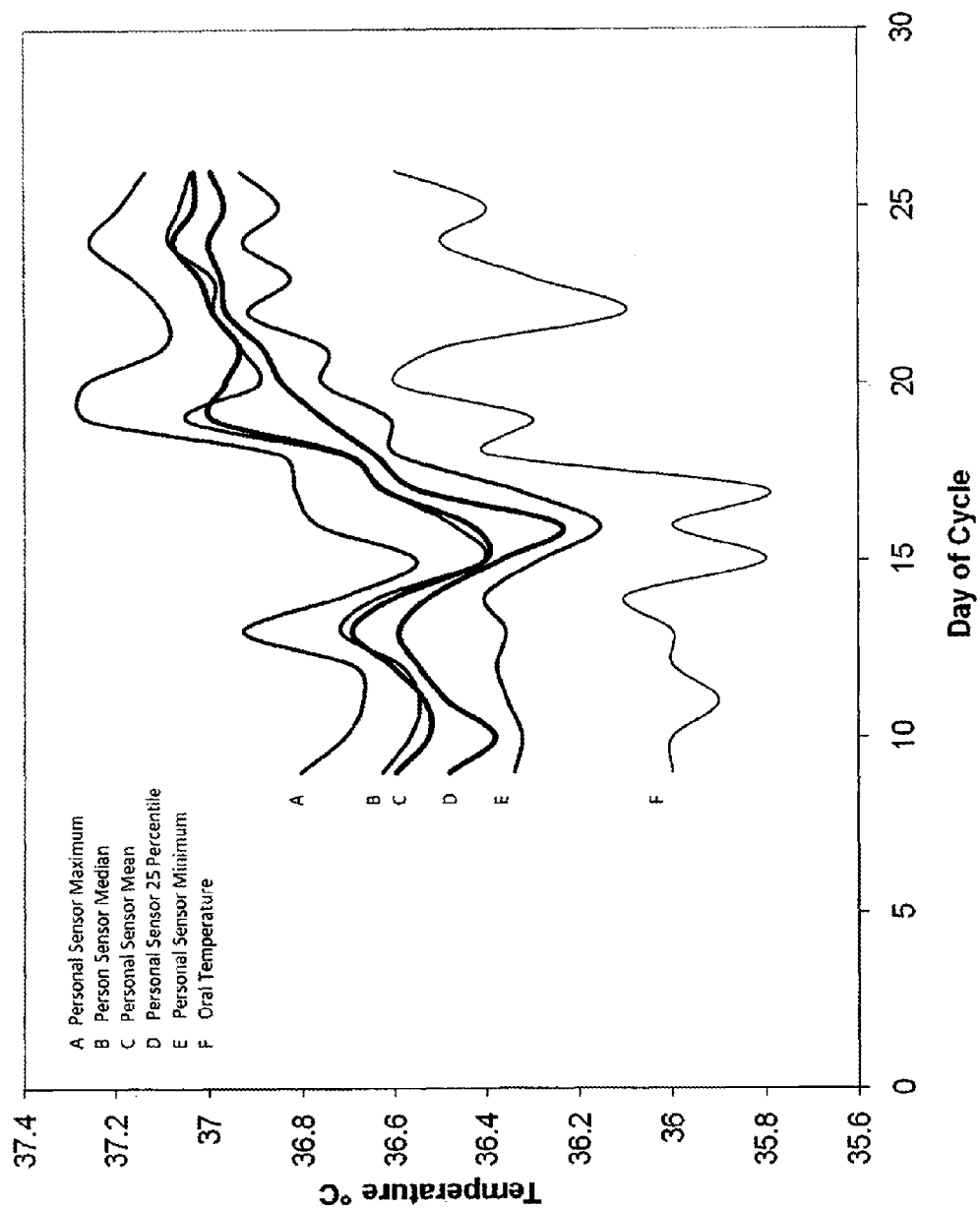
FIG. 3 shows real data obtained from a woman over her complete ovulatory cycle (except for days 0 to 8 during which menstruation took place). Said data has been processed in various ways before being presented in the figure.

Lines A to E of FIG. 3 plot data derived from temperature readings taken every 5 minutes from an indwelling temperature recording device ("personal sensor") placed intravaginally in a woman from day 9 to day 26 of her cycle.

In all cases the reading obtained during overnight periods was processed according to the invention to give a single representative temperature value for each day of the cycle.

Line F plots a once-daily oral temperature reading.

The woman from whom the data was derived was of normal fertility and the cycle shown was an ovulatory cycle. One therefore would expect to see first a temperature slight dip and then a temperature rise as the cycle processes.

Line F shows that the oral temperature readings show a great deal of fluctuation which is because of the influence of erroneous or irrelevant data.

Lines A and E show less of such fluctuations and therefore demonstrate the advantages of taking multiple overnight temperature readings using an indwelling device.

Lines A and E are plotted from representative temperature values that are obtained, respectively, from the maximum and minimum temperature readings obtained during each extended period. It can be seen that in comparison to lines B to D, lines A and E show a high degree of unwanted fluctuations and therefore contrary to what is taught in DE 3342251, the use of maximum and minimum temperature readings as representative temperature values has drawbacks and is not to be preferred.

Lines B, C and D show, respectively, representative temperature values obtained from the median, mean and 25 percentile of the temperature readings in each extended period. It can be seen that the mean, median and 25 percentile are all better representative temperature values over the maximum and minimum, and that the 25 percentile (line D) is better than the other representative values plotted in the graph because it shows fewer fluctuations and corresponds most closely to the woman's true core temperature.

Example 4

Figure 4:
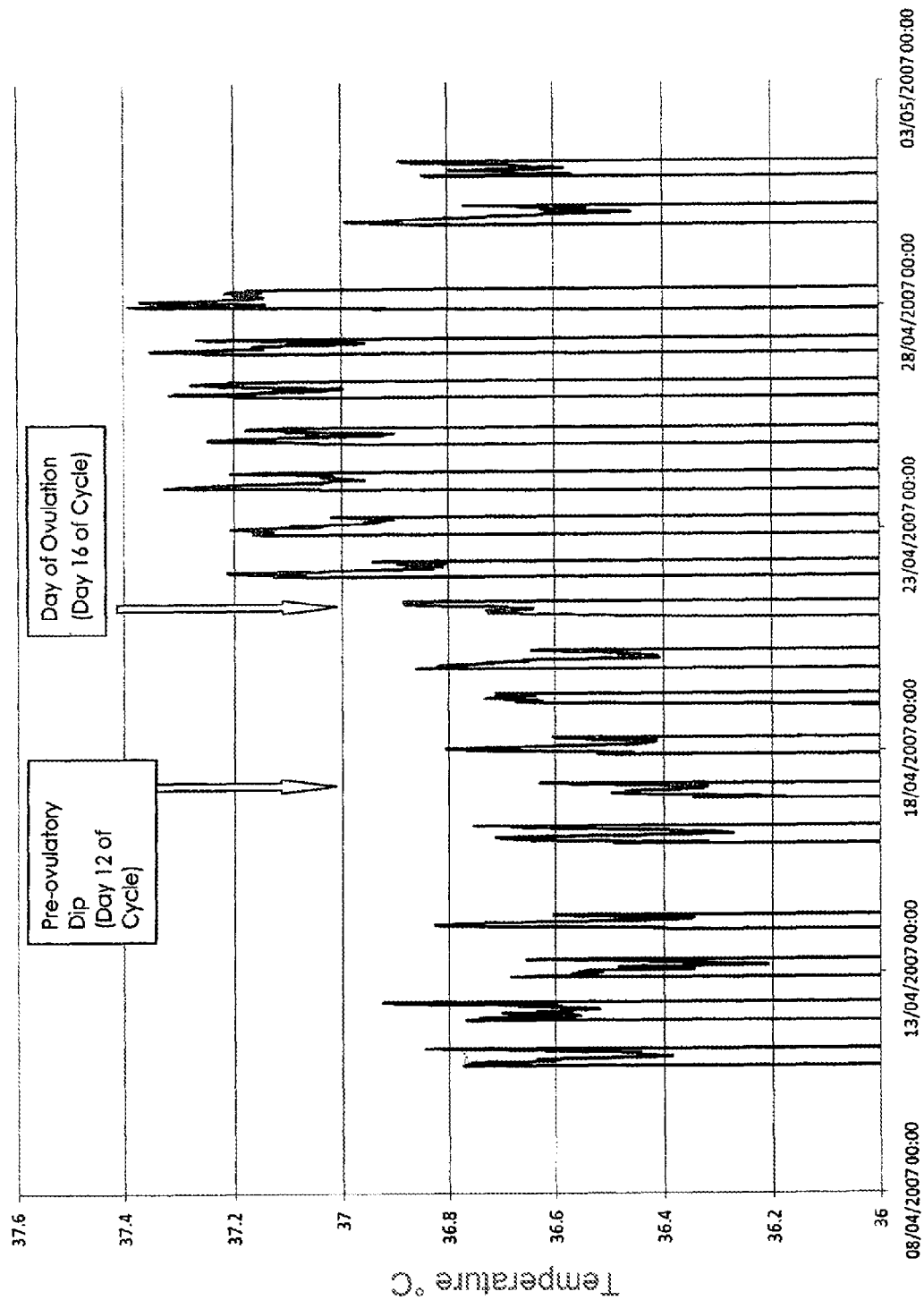
FIG. 4 shows read data obtained from a woman over her complete ovulatory cycle (except for a few days when menstruation took place and a further two days were temperatures were not recorded. During each overnight period temperature was recorded and is shown in the figure.

FIG. 4 shows temperature readings obtained from a woman during overnight time periods spanning a single ovulatory cycle. Ovulation took place at day 16. The temperature readings plotted demonstrate that the method and device of the invention is sufficiently sensitive to detect not only the LH-associated temperature rise but also the pre-ovulatory temperature dip which is associated with a rise in oestradiol levels.

The invention claimed is:

1. A data processing device for processing data indicative of a basal body temperature of a female human user to identify a temperature change event for the female human user, the device comprising:
   a communication interface for receiving multiple body temperature readings or information derived therefrom from multiple female human users, wherein the readings for each user are uniquely identified;
   a processor for identifying temperature readings having one or more characteristics of irrelevant or faulty data and either deleting said readings or labelling them as to be disregarded, for obtaining one or several representative temperature values for each of multiple extended periods, and for analysing the representative temperature values over multiple extended periods to identify a pattern indicative or predictive of ovulation, and wherein the analysis includes using information from values obtained for other female human users;
   wherein the processor is configured to store is arranged to store information relevant to fertility or the timing of ovulation for each user associated with a unique identifier securely on a computer file server for secure retrieval by the user associated with the unique identifier;
   wherein the processor is configured to receive from the user a request for the information,
   wherein the request comprises the unique identifier associated with the user,
   wherein the processor is configured to generate and transmit a signal to cause a display to provide a visible indication of the information for display to the user, and
   wherein the data processing device is configured to store data for multiple cycles for multiple users and performs said analyzing based on said multiple cycles and multiple users.

2. A data processing device according to claim 1 wherein the device is configured to receive supplementary information based on input from the user and to perform said analysing based on said supplementary information.

3. A data processing device according to claim 2 wherein the supplementary information is based on an indication by the user of the onset of menstruation.

4. A data processing device according to claim 2 wherein the supplementary information is based on an indication by the user of a day when the user has a fever.

5. A data processing device according to claim 2 wherein the temperature readings are obtained from a temperature sensor worn by the user and the supplementary information is obtained from a user input device associated with the temperature sensor.

6. A data processing device according to claim 1 wherein the unique identifier for each user is coded into a temperature sensing apparatus associated with the user.

7. A data processing device according to claim 1 wherein the device is configured to analyse readings obtained overnight.

8. A data processing device according to claim 1 wherein the device is configured to analyse historical data of previous cycles and newly obtained data from a current cycle for the user.

9. A data processing device according to claim 1 wherein the device is configured to transmit arranged to transmit a message to a device associated with the user based on said analysis.

10. A data processing device according to claim 1 wherein the information relevant to fertility or the timing of ovulation is available for secure retrieval by a medical practitioner associated with the user.

11. A temperature sensing system comprising; a wearable, removable temperature sensor being arranged to be worn by a female human user for sensing her temperature, being associated with a code for uniquely identifying the user's temperature readings;
    a first an interface for transmitting the temperature readings or information derived therefrom;
    the a user terminal comprising an interface for receiving the temperature readings or information derived therefrom from the temperature sensor;
    a second an interface for transmitting temperature readings or information derived therefrom to a remote server together with the associated unique code to be analysed in conjunction with data from multiple users to determine a pattern indicative or predictive of ovulation for the female human user, the system further including; and
    an input device for receiving an input from the user for indicating supplementary information such as for the onset of menstruation or a fever;
    wherein the temperature sensing system is configured to enable storage of data for multiple cycles for multiple users and performs said analyzing based on said multiple cycles and multiple users.

12. A system according to claim 11 wherein the user terminal is arranged to process temperature readings to delete or flag readings having characteristics of irrelevant or faulty data and to provide readings after said deleting or flagging to the remote server for analysis to identify a pattern indicative of ovulation.

13. A system according to claim 11 wherein the temperature sensor is arranged to be worn overnight by the female human user.

14. A system according to claim 13 wherein the system is selectably removable during the day.

15. A system according to claim 11 wherein the user terminal further comprises an interface for receiving from the remote server an indication relating to ovulation of the female human user, following processing of data from multiple users, and an indicator for communicating the indication to the user.

16. A system according to claim 11 wherein the system is configured to filter arranged to filter the temperature readings so that a subset of the temperature readings, or the information derived therefrom, is transmitted to the remote server.

17. A system according to claim 11 further comprising an interface for accessing from the remote server the pattern indicative or predictive of ovulation after the data has been analysed in conjunction with data from multiple users.

18. A method for processing data indicative of a basal body temperature of a female human user to identify a temperature change event for the female human user, the method comprising:
    receiving multiple body temperature readings or information derived therefrom from multiple female human users, wherein the readings for each user are uniquely identified;
    identifying temperature readings having one or more characteristics of irrelevant or faulty data and either deleting said readings or labelling them as to be disregarded;

obtaining one or several representative temperature values for each of multiple extended periods;

analysing the representative temperature values over multiple extended periods and information from values obtained for other female human users to identify a pattern indicative or predictive of ovulation;

storing information relevant to fertility or the timing of ovulation for each user associated with a unique identifier securely on a computer file server for secure retrieval by the user associated with the unique identifier;

receiving from the user a request for the information, wherein the request comprises the unique identifier associated with the user;

generating and transmitting a signal to cause an interface to provide a visible indication of the information for display to the user; and storing data for multiple cycles for multiple users and performing said analyzing based on the multiple cycles and multiple users.

* * * * *